(12) United States Patent
Hatta et al.

(10) Patent No.: US 11,421,172 B2
(45) Date of Patent: Aug. 23, 2022

(54) FLUOROPOLYETHER COMPOUND, LUBRICANT USING SAME, AND USAGE THEREOF

(71) Applicant: Moresco Corporation, Kobe (JP)

(72) Inventors: Tomomi Hatta, Kobe (JP); Tsuyoshi Shimizu, Kobe (JP); Aya Inoue, Kobe (JP); Yasuo Sakane, Kobe (JP)

(73) Assignee: Moresco Corporation, Kobe (JP)

( * ) Notice: Subject to any disclaimer, the term of this patent is extended or adjusted under 35 U.S.C. 154(b) by 445 days.

(21) Appl. No.: 16/482,756

(22) PCT Filed: Jan. 17, 2018

(86) PCT No.: PCT/JP2018/001133
§ 371 (c)(1),
(2) Date: Aug. 1, 2019

(87) PCT Pub. No.: WO2018/147017
PCT Pub. Date: Aug. 16, 2018

(65) Prior Publication Data
US 2019/0352573 A1    Nov. 21, 2019

(30) Foreign Application Priority Data

Feb. 10, 2017    (JP) .............................. JP2017-023641

(51) Int. Cl.
*C10M 107/38*    (2006.01)
*C08G 65/22*    (2006.01)
(Continued)

(52) U.S. Cl.
CPC ......... *C10M 107/38* (2013.01); *C08G 65/226* (2013.01); *G11B 5/7257* (2020.08); *C10M 2213/0606* (2013.01); *C10N 2040/18* (2013.01)

(58) Field of Classification Search
CPC ................ G11B 5/725; C10M 107/38; C10M 2213/0606; C10M 2213/00;
(Continued)

(56) References Cited

U.S. PATENT DOCUMENTS 3,549,591 A    12/1970 Griffith
3,720,639 A    3/1973 Griffith
(Continued)

FOREIGN PATENT DOCUMENTS

JP    2006070173 A    3/2006
JP    2009211765 A    9/2009
(Continued)

OTHER PUBLICATIONS

Notification of Reasons for Refusal issued in JP Counterpart Application No. 2018-566813 dated Mar. 31, 2020.
(Continued)

*Primary Examiner* — Holly Rickman
(74) *Attorney, Agent, or Firm* — Harness Dickey & Pierce P.L.C.

(57) ABSTRACT

Provided are a lubricant that is highly resistant to contamination and highly thermally stable, a lubricant that is highly durable and highly heat resistant, and a magnetic disk. A fluoropolyether compound contains perfluoropolyether groups, end groups each containing at least one hydroxyl group, and a linking group that is comprised of a $C_4$-$C_{14}$ hydrocarbon group and that contains at least one hydroxyl group.

6 Claims, 1 Drawing Sheet

(51) Int. Cl.
*G11B 5/725* (2006.01)
*C10N 40/18* (2006.01)

(58) Field of Classification Search
CPC ........ C10M 2213/04; C10M 2213/043; C10M 2213/06; C08G 65/226; C08G 65/007; C10N 2040/18; C07C 43/13; C07C 43/23; C07C 43/135; C07C 43/137; C07C 43/225
See application file for complete search history.

(56) References Cited

U.S. PATENT DOCUMENTS

| | | | |
|---|---|---|---|
| 10,047,317 B2* | 8/2018 | Sagata | C10M 105/54 |
| 2012/0127599 A1 | 5/2012 | Shimokawa et al. | |
| 2012/0315504 A1 | 12/2012 | Shimizu et al. | |
| 2013/0315620 A1 | 11/2013 | Kikuchi et al. | |
| 2015/0235664 A1* | 8/2015 | Deng | G11B 5/8408 360/75 |
| 2016/0055874 A1 | 2/2016 | Shimokawa et al. | |
| 2016/0260452 A1 | 9/2016 | Pathem | |
| 2017/0260472 A1 | 9/2017 | Sagata et al. | |
| 2018/0268853 A1 | 9/2018 | Shimokawa et al. | |

FOREIGN PATENT DOCUMENTS

| | | |
|---|---|---|
| JP | 2009301709 A | 12/2009 |
| JP | 2010086598 A | 4/2010 |
| JP | 2010231857 A | 10/2010 |
| JP | 2010282707 A | 12/2010 |
| JP | 2013018961 A | 1/2013 |
| JP | 2013134369 A | 7/2013 |
| WO | 2010038773 A1 | 4/2010 |
| WO | 2016084781 A1 | 6/2016 |
| WO | 2017145995 A1 | 8/2017 |

OTHER PUBLICATIONS

International Search Report from PCT Application No. PCT/JP2018/001133 dated Apr. 17, 2018.
International Preliminary Report on Patentability for PCT Application No. PCT/JP2018/001133 dated Aug. 22, 2019.

* cited by examiner (a)

(b)

FLUOROPOLYETHER COMPOUND, LUBRICANT USING SAME, AND USAGE THEREOF

TECHNICAL FIELD

The present invention relates to a fluoropolyether compound, a lubricant containing the fluoropolyether compound, and usage thereof.

BACKGROUND ART

Many of the existing magnetic disks are constituted by: a recording layer disposed on a substrate; a protective layer disposed on the recording layer in order to protect information recorded on the recording layer; and a lubricant layer disposed on the protective layer.

With the increasing recording density of magnetic disks in recent years, the distance between a magnetic head and the surface of a magnetic disk has decreased to the order of ten nanometers to read data from very small magnetic domains. Therefore, a lubricant for use in the lubricant layer is required to have long-term stability, chemical resistance, and the like characteristics even after formed into a thin film.

Patent Literature 1 discloses using the following fluoropolyether compound as a lubricant that meets the above demands and that maintains its lubricity even in heat-assisted magnetic recording (HAMR), in which a recording spot is heated by laser irradiation immediately before writing. That is, Patent Literature 1 discloses using a fluoropolyether compound in which an aliphatic hydrocarbon chain with a specific number of carbon atoms present in the middle of a molecule is ether-linked to perfluoropolyethers.

CITATION LIST

Patent Literature

[Patent Literature 1]
International Publication No. WO 2016/084781 (Publication date: Jun. 2, 2016)

SUMMARY OF INVENTION

Technical Problem

The lubricant disclosed in Patent Literature 1 is highly heat resistant, but is required to be more heat resistant. Furthermore, if the lubricant layer becomes thinner, such a thin lubricant layer is not capable of sufficiently covering the protective layer therebelow, and the protective layer becomes more prone to impurity contamination. There is also a tendency that if the protective layer is contaminated with impurities, the magnetic disk becomes less durable.

An object of an aspect of the present invention is to provide a lubricant that is highly resistant to contamination and highly resistant to heat. An object of another aspect of the present invention is to provide a magnetic disk that includes the lubricant and that is highly durable and highly heat resistant.

Solution to Problem

The inventors of the present invention studied hard to attain the above objects, and found that it is possible to provide a lubricant that is highly resistant to contamination and highly resistant to heat by using a fluoropolyether compound that contains: perfluoropolyether groups; end groups each of which contains at least one hydroxyl group; and a linking group that is comprised of a $C_4$-$C_{14}$ hydrocarbon group and that contains at least one hydroxyl group. On the basis of this finding, the inventors accomplished the present invention. Specifically, the present invention includes the following arrangements.

[1] A fluoropolyether compound having a structure represented by Formula (1) below:

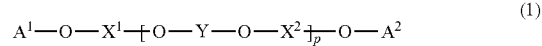

(1)

where $X^1$ and $X^2$ represent perfluoropolyether groups,
$A^1$ and $A^2$ each represent an end group containing at least one hydroxyl group,
Y represents a linking group that is comprised of a $C_4$-$C_{14}$ hydrocarbon group and that contains at least one hydroxyl group, and at least one carbon atom in a main chain of the $C_4$-$C_{14}$ hydrocarbon group is optionally substituted with an oxygen atom, and
p is a real number of 2 or more.

[2] The fluoropolyether compound according to [1], wherein p in Formula (1) is a real number of 2 to 10.

[3] The fluoropolyether compound according to [1] or [2], wherein $X^1$ and $X^2$ in Formula (1) independently represent —$CH_2(CF_2)_qO(CF_2O)_x(CF_2CF_2O)_y(CF_2CF_2CF_2O)_z$ $(CF_2CF_2CF_2CF_2O)_w(CF_2)_qCH_2$—, where x and y are each a real number of 0 to 30, z is a real number of 0 to 30, w is a real number of 0 to 20, and q is an integer of 1 to 3.

[4] The fluoropolyether compound according to any one of [1] to [3], wherein the linking group has a structure represented by Formula (2) below:

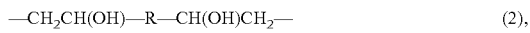

(2), where R represents a $C_1$-$C_6$ aliphatic hydrocarbon group or a $C_6$-$C_{10}$ hydrocarbon group whose main chain contains a phenylene group, at least one carbon atom in the main chain, which contains a phenylene group, of the $C_6$-$C_{10}$ hydrocarbon group is optionally substituted with an oxygen atom.

[5] The fluoropolyether compound according to any one of [1] to [4], wherein $A^1$ and $A^2$ in Formula (1) independently represent —OH, —$CH_2CH(OH)CH_2OH$, —$OCH_2CH(OH)CH_2OCH_2CH(OH)CH_2OH$, —$O(CH_2)_m$OH, or —$OCH_2CH(OH)CH_2$—$OC_6H_4$—$R^1$, where m is an integer of 2 to 8 and $R^1$ is hydrogen, a $C_1$-$C_4$ alkoxy group, an amino group, or an amide residue.

[6] A fluoropolyether compound having a structure represented by any of Formulas (3) to (6) below:

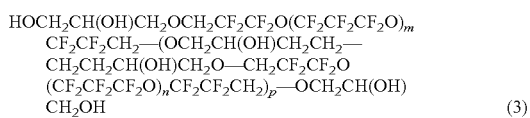

(3)

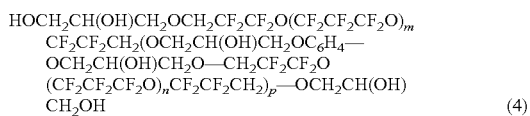

(4)

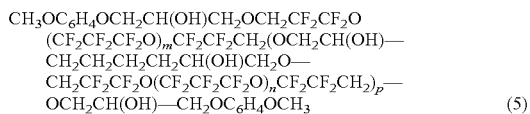

(5)

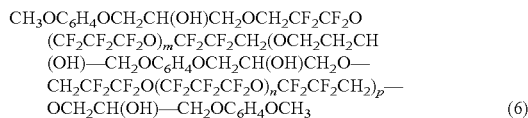

CH₃OC₆H₄OCH₂CH(OH)CH₂OCH₂CF₂CF₂O
(CF₂CF₂CF₂O)$_m$CF₂CF₂CH₂(OCH₂CH₂CH
(OH)—CH₂OC₆H₄OCH₂CH(OH)CH₂O—
CH₂CF₂CF₂O(CF₂CF₂CF₂O)$_n$CF₂CF₂CH₂)$_p$—
OCH₂CH(OH)—CH₂OC₆H₄OCH₃  (6)

where n is a real number of 0 to 30, m is a real number of 0 to 30, and p is a real number of 2 to 10.

[7] A lubricant containing a fluoropolyether compound recited in any one of [1] to [6].

[8] A magnetic disk including: a recording layer; a protective layer disposed on the recording layer; and a lubricant layer disposed on the protective layer,
the lubricant layer containing a lubricant recited in [7].

[9] A method of producing a magnetic disk that includes: a recording layer; a protective layer disposed on the recording layer; and a lubricant layer disposed on the protective layer,
the method including a step of forming the lubricant layer by placing a lubricant recited in [7] on an exposed surface of the protective layer of a stack of the recording layer and the protective layer.

Advantageous Effects of Invention

According to a fluoropolyether compound in accordance with an aspect of the present invention, not only the terminals of a molecule but also hydroxyl and aromatic groups contained in the linking group serve to cover functional groups of a protective layer, and thereby a plurality of functional groups of the protective layer can be covered by a single molecule. This makes it possible to efficiently cover the protective layer. Therefore, a lubricant that contains a fluoropolyether compound in accordance with an aspect of the present invention provides the following effects: high contaminant resistance and high heat resistance. The following effect is also provided: use of a lubricant in accordance with an aspect of the present invention improves the durability and heat resistance of a magnetic disk.

DESCRIPTION OF EMBODIMENTS

Figure 1:
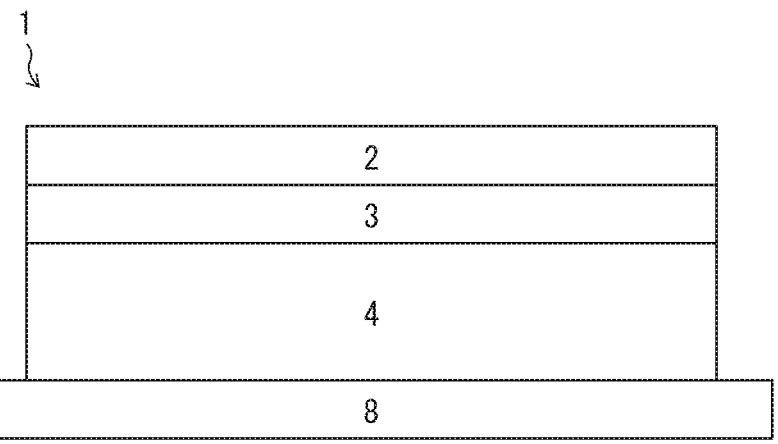
FIG. 1 shows cross-sectional views illustrating structures of magnetic disks in accordance with embodiments of the present invention.
Figure 1:
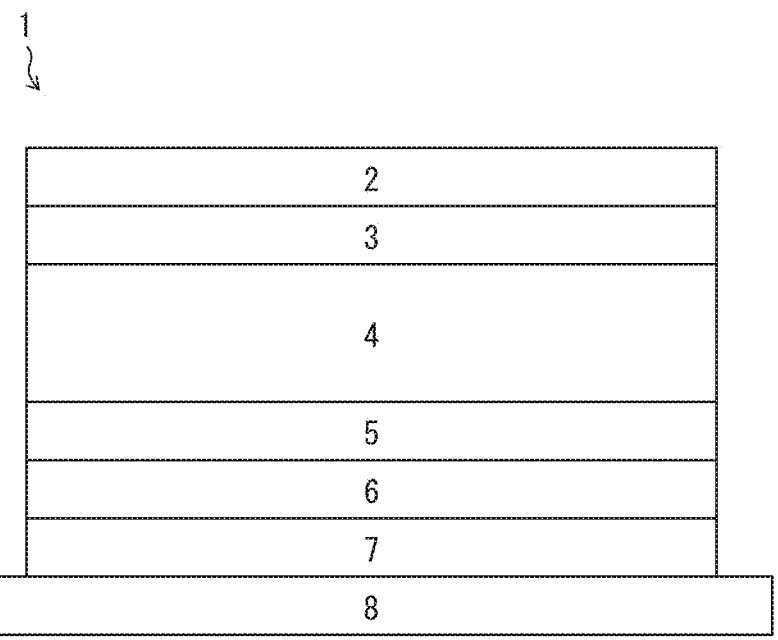

The following description will discuss embodiments of the present invention in detail. Note, however, that the present invention is not limited to the following embodiments, but can be altered within this disclosure. The present invention also encompasses, in its technical scope, any embodiment derived by combining technical means disclosed in differing embodiments. Note that the expression "A to B", representing a numerical range, herein means "not less than A and not more than B" unless otherwise specified in this specification.

(I) Fluoropolyether Compound

A fluoropolyether compound in accordance with an embodiment of the present invention has a structure represented by Formula (1) below:

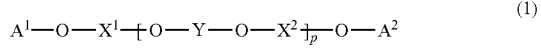

where $X^1$ and $X^2$ represent perfluoropolyether groups, $A^1$ and $A^2$ each represent an end group containing at least one hydroxyl group, Y represents a linking group that is comprised of a $C_4$-$C_{14}$ hydrocarbon group and that contains at least one hydroxyl group, at least one carbon atom in the main chain of the hydrocarbon group is optionally substituted with an oxygen atom, and $p \geq 2$.

In Formula (1), $X^1$ and $X^2$ represent perfluoropolyether groups.

It is more preferable that $X^1$ and $X^2$ in Formula (1) independently represent —CH₂(CF₂)$_q$O(CF₂O)$_x$(CF₂CF₂O)$_y$(CF₂CF₂CF₂O)$_z$(CF₂CF₂CF₂CF₂O)$_w$(CF₂)$_q$CH₂— (x and y are each a real number of 0 to 30, z is a real number of 0 to 30, w is a real number of 0 to 20, and q is an integer of 1 to 3).

x and y are each more preferably a real number of 0 to 20, even more preferably a real number of 0 to 12, particularly preferably a real number of 2 to 8. When x and y are each a real number of 0 to 30, the molecular chain of the fluoropolyether compound becomes more flat, making it possible to form a thin film of a lubricant that contains the fluoropolyether compound. Thus, it is preferable that x and y are each a real number of 0 to 30.

z is more preferably a real number of 1 to 20, even more preferably a real number of 1 to 12, particularly preferably a real number of 2 to 8. When z is a real number of 0 to 30, the molecular chain of the fluoropolyether compound becomes more flat, making it possible to form a thin film of a lubricant that contains the fluoropolyether compound. Thus, it is preferable that z is a real number of 0 to 30.

w is more preferably a real number of 0 to 15, even more preferably a real number of 1 to 10, particularly preferably a real number of 1 to 5. When w is a real number of 0 to 20, the molecular chain of the fluoropolyether compound becomes more flat, making it possible to form a thin film of a lubricant that contains the fluoropolyether compound. Thus, it is preferable that w is a real number of 0 to 20.

In Formula (1), $A^1$ and $A^2$ each represent an end group containing at least one hydroxyl group. $A^1$ and $A^2$ may be any end groups, provided that each of them contains at least one hydroxyl group. $A^1$ and $A^2$ may contain an aromatic group.

It is preferable that $A^1$ and $A^2$ in Formula (1) independently represent —OH, —CH₂CH(OH)CH₂OH, —OCH₂CH(OH)CH₂OCH₂CH(OH)CH₂OH, —O(CH₂)$_m$OH, or —OCH₂CH(OH)CH₂—OC₆H₄—$R^1$ (where m is an integer of 2 to 8 and $R^1$ is hydrogen, a $C_1$-$C_4$ alkoxy group, an amino group, or an amide residue).

In Formula (1), Y represents a linking group that is comprised of a $C_4$-$C_{14}$ hydrocarbon group and that contains at least one hydroxyl group. At least one carbon atom in a main chain of the hydrocarbon group is optionally substituted with an oxygen atom.

The hydrocarbon group may be an aliphatic hydrocarbon group or an aromatic-containing hydrocarbon group.

The aliphatic hydrocarbon group may either be a linear aliphatic hydrocarbon group or a branched aliphatic hydrocarbon group. In a case where Y is a linear aliphatic hydrocarbon group, both terminals of the hydrocarbon group are each linked to $X^1$ or $X^2$ through an oxygen atom. In a case where Y is a branched aliphatic hydrocarbon group, both terminals of the main chain of the hydrocarbon group are each linked to $X^1$ or $X^2$ through an oxygen atom. The hydrocarbon group is preferably a linear hydrocarbon group, because this gives a more flat molecular chain of the fluoropolyether compound and makes it possible to form a thin film of a lubricant that contains the fluoropolyether compound. The aliphatic hydrocarbon group may be a saturated hydrocarbon group or may be an unsaturated hydrocarbon group.

In a case where the hydrocarbon group is an aromatic-containing hydrocarbon group, the aromatic group may be contained in the main chain or may be contained in a side chain. Examples of the aromatic group include phenylene and phenyl groups.

The hydrocarbon group is preferably a $C_4$-$C_{14}$ hydrocarbon group, more preferably a $C_4$-$C_{10}$ hydrocarbon group, even more preferably a $C_4$-$C_8$ hydrocarbon group. When the hydrocarbon group is a $C_4$-$C_{14}$ hydrocarbon group, the fluorine properties of the compound improve and, in turn, surface energy decreases and contamination resistance improves. Thus, it is preferable that the hydrocarbon group is a $C_4$-$C_{14}$ hydrocarbon group.

At least one carbon atom in the main chain of the hydrocarbon group is optionally substituted with an oxygen atom. In particular, in a case where the hydrocarbon group contains an aromatic group, it is more preferable that at least one carbon atom in the main chain of the hydrocarbon group is substituted with an oxygen atom. In a case where the hydrocarbon group is an aliphatic hydrocarbon group, it is more preferable that such at least one carbon atom in the main chain of the hydrocarbon group is not substituted with an oxygen atom.

In a fluoropolyether compound in accordance with an embodiment of the present invention, Y may have a structure represented by Formula (2) below:

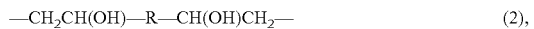

—CH$_2$CH(OH)—R—CH(OH)CH$_2$—  (2), where R represents a $C_1$-$C_6$ aliphatic hydrocarbon group or a $C_6$-$C_{10}$ hydrocarbon group whose main chain contains a phenylene group, and at least one carbon atom in the main chain, which contains a phenylene group, of the $C_6$-$C_{10}$ hydrocarbon group is optionally substituted with an oxygen atom. When Y has a structure represented by Formula (2), the number of hydroxyl groups and aromatic groups contained in the linking group increases, making it possible to cover a plurality of functional groups in the protective layer by a single molecule and thus possible to efficiently cover the protective layer. Thus, it is preferable that Y has a structure represented by Formula (2). In a case where R is a $C_1$-$C_6$ aliphatic hydrocarbon group, R may be saturated or unsaturated, and may be a linear group or a branched group. Examples of the $C_1$-$C_6$ aliphatic hydrocarbon group include linear saturated $C_1$-$C_6$ hydrocarbon groups and branched saturated $C_1$-$C_6$ hydrocarbon groups. In a case where R is a $C_6$-$C_{10}$ hydrocarbon group whose main chain contains a phenylene group, an example of such R is —CH$_2$—O—C$_6$H$_4$—O—CH$_2$— or the like.

Y in Formula (1) may be any linking group, provided that it contains at least one hydroxyl group. Y contains preferably one or more hydroxyl groups, more preferably two or more hydroxyl groups. When Y contains at least one hydroxyl group, the number of hydroxyl groups contained in the linking group increases, making it possible to cover a plurality of functional groups in the protective layer by a single molecule and thus possible to efficiently cover the protective layer. Thus, it is preferable that Y contains at least one hydroxyl group.

In a fluoropolyether compound in accordance with an embodiment of the present invention, p in Formula (1) is a real number of 2 or more. In Formula (1), p is preferably a real number of 2 to 10, more preferably a real number of 3 to 5. When p falls within the above range, the number of hydroxyl and aromatic groups contained in a single fluoropolyether compound molecule increases, making it possible to cover a plurality of functional groups in the protective layer by a single molecule and thus possible to efficiently cover the protective layer. Thus, it is preferable that p falls within the above range. A lubricant containing the fluoropolyether compound, which is capable of efficiently covering the protective layer, provides the following effects: high contamination resistance, high thermal stability, and high heat resistance. It is preferable that p falls within the above range also because such a fluoropolyether compound can be easily synthesized.

A fluoropolyether compound in accordance with an embodiment of the present invention is not limited to a particular kind, and X, Y, and A in Formula (1) may each be any of the foregoing examples, provided that the fluoropolyether compound is a compound represented by Formula (1). More specific examples of the fluoropolyether compound include compounds each having a structure represented by any of Formulas (3) to (6) below.

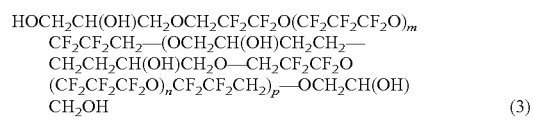

HOCH$_2$CH(OH)CH$_2$OCH$_2$CF$_2$CF$_2$O(CF$_2$CF$_2$CF$_2$O)$_m$
CF$_2$CF$_2$CH$_2$—(OCH$_2$CH(OH)CH$_2$CH$_2$—
CH$_2$CH$_2$CH(OH)CH$_2$O—CH$_2$CF$_2$CF$_2$O
(CF$_2$CF$_2$CF$_2$O)$_n$CF$_2$CF$_2$CH$_2$)$_p$—OCH$_2$CH(OH)
CH$_2$OH  (3)

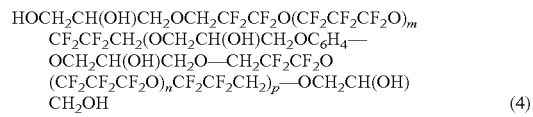

HOCH$_2$CH(OH)CH$_2$OCH$_2$CF$_2$CF$_2$O(CF$_2$CF$_2$CF$_2$O)$_m$
CF$_2$CF$_2$CH$_2$(OCH$_2$CH(OH)CH$_2$OC$_6$H$_4$—
OCH$_2$CH(OH)CH$_2$O—CH$_2$CF$_2$CF$_2$O
(CF$_2$CF$_2$CF$_2$O)$_n$CF$_2$CF$_2$CH$_2$)$_p$—OCH$_2$CH(OH)
CH$_2$OH  (4)

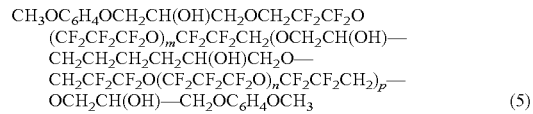

CH$_3$OC$_6$H$_4$OCH$_2$CH(OH)CH$_2$OCH$_2$CF$_2$CF$_2$O
(CF$_2$CF$_2$CF$_2$O)$_m$CF$_2$CF$_2$CH$_2$(OCH$_2$CH(OH)—
CH$_2$CH$_2$CH$_2$CH$_2$CH(OH)CH$_2$O—
CH$_2$CF$_2$CF$_2$O(CF$_2$CF$_2$CF$_2$O)$_n$CF$_2$CF$_2$CH$_2$)$_p$—
OCH$_2$CH(OH)—CH$_2$OC$_6$H$_4$OCH$_3$  (5)

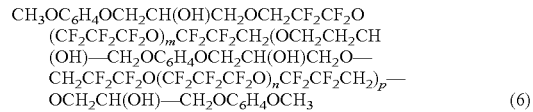

CH$_3$OC$_6$H$_4$OCH$_2$CH(OH)CH$_2$OCH$_2$CF$_2$CF$_2$O
(CF$_2$CF$_2$CF$_2$O)$_m$CF$_2$CF$_2$CH$_2$(OCH$_2$CH$_2$CH
(OH)—CH$_2$OC$_6$H$_4$OCH$_2$CH(OH)CH$_2$O—
CH$_2$CF$_2$CF$_2$O(CF$_2$CF$_2$CF$_2$O)$_n$CF$_2$CF$_2$CH$_2$)$_p$—
OCH$_2$CH(OH)—CH$_2$OC$_6$H$_4$OCH$_3$  (6)

In Formulas (3) to (6), n is a real number of 0 to 30, m is a real number of 0 to 30, and p is a real number of 2 to 10.

A method of producing a fluoropolyether compound in accordance with an embodiment of the present invention is not limited to a particular kind. An example thereof is a method that includes the steps of (i) obtaining, from a perfluoropolyether compound whose perfluoropolyether group has hydroxyl groups at both terminals thereof, a mixture of the perfluoropolyether compound and another perfluoropolyether compound whose perfluoropolyether group has one hydroxyl group originating from the perfluoropolyether compound (source material) at one terminal thereof and has a hydroxyl-containing end group linked to the other terminal thereof, and (ii) synthesizing a fluoropolyether compound in accordance with an embodiment of the present invention by allowing the mixture obtained in step (i) to react with a compound in which the foregoing linking group has, at both terminals thereof, structures linkable by reaction with the hydroxyl groups at the terminals of the mixture obtained in step (i).

The following description will discuss steps (i) and (ii).

Step (i) is to obtain, from a perfluoropolyether compound whose perfluoropolyether group has hydroxyl groups at both terminals thereof, a mixture of the perfluoropolyether compound and another perfluoropolyether compound whose perfluoropolyether group has one hydroxyl group originating from the perfluoropolyether compound (source material)

at one terminal thereof and has a hydroxyl-containing end group linked to the other terminal thereof.

In step (i), the perfluoropolyether compound (source material) is preferably a compound represented by $HOCH_2(CF_2)_qO(CF_2O)_x(CF_2CF_2O)_y(CF_2CF_2CF_2O)_z(CF_2CF_2CF_2CF_2O)_w(CF_2)_qCH_2OH$ (x and y each represent a real number of 0 to 30, z is a real number of 0 to 30, w is a real number of 0 to 20, and q is an integer of 1 to 3).

The perfluoropolyether compound (source material) preferably has a number average molecular weight of 150 to 6000, more preferably 500 to 2500, even more preferably 600 to 1000.

In step (i), the mixture of perfluoropolyether compounds can be obtained by, for example, allowing the perfluoropolyether compound (source material) to react with an end group precursor compound in which the foregoing end group ($A^1$ or $A^2$ in Formula (1)) has at its terminal a structure linkable by reaction with the hydroxyl group at a terminal of the perfluoropolyether compound. In this method, the amount of the end group precursor compound is preferably 20% by mole to 160% by mole, more preferably 30% by mole to 80% by mole, relative to the perfluoropolyether compound. Provided that the amount of the end group precursor compound falls within the above range, a desired fluoropolyether compound can be obtained.

Examples of the compound in which the foregoing end group ($A^1$ or $A^2$ in Formula (1)) has at its terminal a structure linkable by reaction with the hydroxyl group at a terminal of the perfluoropolyether compound include: compounds having an epoxide structure at a terminal thereof; and haloalkyl alcohols represented by $XCH_2CH(OH)CH_2OH$ (where X represents a halogen atom).

Examples of compounds having an epoxide structure at a terminal thereof include glycidol, propylene oxide, glycidyl methyl ether, and isobutylene oxide.

It is preferable that a solvent is used in step (i). Examples of the solvent include t-butyl alcohol, dimethyl formaldehyde, 1,4-dioxane, meta-xylene hexafluoride, dimethyl sulfoxide, and dimethylacetamide.

It is also preferable that a reaction accelerator is used in step (i). Examples of the reaction accelerator include sodium t-butoxide, potassium t-butoxide, sodium hydroxide, potassium hydroxide, and sodium hydride.

In step (i), the perfluoropolyether compound (source material) and the end group precursor compound are allowed to react at a temperature of preferably 50° C. to 120° C., more preferably 60° C. to 70° C. The reaction time is preferably 1 hour to 96 hours, more preferably 20 hours to 25 hours.

The reaction product of the perfluoropolyether compound (source material) and the end group precursor compound is, for example, washed with water, dehydrated, and then purified by silica gel column chromatography or the like, and thereby the mixture stated in step (i) can be obtained.

Step (ii) is to synthesize a fluoropolyether compound in accordance with an embodiment of the present invention by allowing the mixture obtained in step (i) to react with a linking group precursor compound in which the foregoing linking group (Y in Formula (1)) has, at both terminals thereof, structures linkable by reaction with the hydroxyl groups at the terminals of the mixture obtained in step (i).

Examples of the linking group precursor compound (source material) include: diepoxide compounds in which the linking group (Y in Formula (1)) has epoxide structures at both terminals thereof; and α,ω-dihaloalkyl alcohol compounds. Examples of diepoxide compounds include 1,3-butadiene diepoxide, 1,4-pentadiene diepoxide, 1,5-hexadiene diepoxide, 1,6-heptadiene diepoxide, 1,7-octadiene diepoxide, 1,8-nonadiene diepoxide, 1,9-decadiene diepoxide, catechol diglycidyl ether, resorcinol diglycidyl ether, and hydroquinone diglycidyl ether. The amount of the linking group precursor compound here is preferably 40% by mole to 280% by mole, more preferably 80% by mole to 240% by mole, relative to the perfluoropolyether compound. Provided that the amount of the linking group precursor compound falls within the above range, a desired fluoropolyether compound can be obtained.

It is preferable that any of the foregoing solvents, any of the foregoing reaction accelerators, and/or the like are used in step (ii), as with step (i).

In step (ii), the mixture obtained in step (i) and the linking group precursor compound (source material) are allowed to react at a temperature of preferably 50° C. to 120° C., more preferably 60° C. to 70° C. The reaction time is preferably 1 hour to 196 hours, preferably 24 hours to 48 hours.

The reaction product of the mixture obtained in step (i) and the linking group precursor compound (source material) is, for example, washed with water, dehydrated, and then purified by silica gel column chromatography or the like, and thereby the fluoropolyether compound in accordance with an embodiment of the present invention can be obtained.

Note that the fluoropolyether compound can alternatively be produced by allowing a perfluoropolyether compound (source material) and a linking group precursor compound (source material) to react with each other without going through the mixture stated in step (i).

Step (i) and step (ii) do not have to be carried out in the above-described order; alternatively, step (i) may be carried out after step (ii).

(II) Lubricant

A lubricant in accordance with an embodiment of the present invention is not limited to a particular kind, provided that the lubricant contains a fluoropolyether compound in accordance with an embodiment of the present invention.

With regard to a lubricant, a fluoropolyether compound in accordance with an embodiment of the present invention may be used alone as a lubricant. Alternatively, a fluoropolyether compound in accordance with an embodiment of the present invention and some other component mixed at a certain ratio may be used as a lubricant, provided that the performance of the fluoropolyether compound is not impaired.

Examples of the above-described other component include: known lubricants for magnetic disks such as Fomblin Zdol (available from Solvay Solexis), Ztetraol (available from Solvay Solexis), and Demnum (available from Daikin Industries, Ltd.); and PHOSFAROL A20H (available from MORESCO Corporation).

(III) Magnetic Disk

A magnetic disk in accordance with an embodiment of the present invention includes, as illustrated in (a) of FIG. 1, a recording layer 4, a protective film layer (protective layer) 3, and a lubricant layer 2, which are disposed on a non-magnetic substrate 8. The magnetic disk is not limited to a particular kind, provided that the lubricant layer 2 contains the foregoing lubricant.

In another embodiment, a magnetic disk can include, like a magnetic disk 1 illustrated in (b) of FIG. 1, a lower layer 5 that underlies the recording layer 4, one or more soft magnetic lower layers 6 that underlie the lower layer 5, and an adhesive layer 7 that underlies the one or more soft magnetic lower layers 6. In one embodiment, all these layers can be formed on the non-magnetic substrate 8, which can contain glass. Each of the layers of the magnetic disk 1 other than the lubricant layer 2 can contain a material that is known in this technical field to be suitable for a corresponding layer of a magnetic disk.

(IV) Method of Producing Magnetic Disk

A method of producing a magnetic disk in accordance with an embodiment of the present invention includes a step of forming a lubricant layer by placing a lubricant in accordance with an embodiment of the present invention on the exposed surface of a protective layer of a stack of a recording layer and the protective layer.

There is no particular limitation on a method of forming a lubricant layer by placing the lubricant on the exposed surface of a protective layer of a stack of a recording layer and the protective layer.

It is preferable that a lubricant is placed on the exposed surface of a protective layer by the following method: the lubricant is diluted with a solvent and then placed on the exposed surface. Examples of the solvent include: PF-5060, PF-5080, HFE-7100, and HFE-7200 available from 3M; and Vertrel-XF (registered trademark) available from DuPont. The lubricant diluted with a solvent has a concentration of preferably 0.001 wt % to 1 wt %, more preferably 0.005 wt % to 0.5 wt %, even more preferably 0.01 wt % to 0.1 wt %. When the concentration of the lubricant diluted with a solvent is 0.001 wt % to 1 wt %, the viscosity of the lubricant is low enough to easily control the thickness of the lubricant layer; thus, it is preferable that the concentration of the diluted lubricant is 0.001 wt % to 1 wt %.

The following arrangement may be employed: the recording layer and the protective layer are formed in this order; the lubricant is placed on the exposed surface of the protective layer; and then ultraviolet irradiation or heat treatment is carried out.

Carrying out ultraviolet irradiation or heat irradiation forms stronger bonds between the lubricant layer and the exposed surface of the protective layer and, in turn, prevents the lubricant from evaporating from heat. Thus, it is preferable that ultraviolet irradiation or heat irradiation is carried out. When carrying out ultraviolet irradiation, it is preferable to use an ultraviolet ray having a wavelength of 185 nm or 254 nm as the dominant wavelength, in order to activate the exposed surface of the protective layer without affecting deep areas of the lubricant layer and the protective layer. The temperature of the heat treatment is preferably 60° C. to 170° C., more preferably 80° C. to 170° C., even more preferably 80° C. to 150° C.

The present invention is not limited to the embodiments, but can be altered by a skilled person in the art within the scope of the claims. The present invention also encompasses, in its technical scope, any embodiment derived by combining technical means disclosed in differing embodiments.

EXAMPLES

The following description will more specifically discuss the present invention based on Examples; however, the present invention is not limited to the following Examples. In the following Examples, siloxane resistance and heat resistance were evaluated in the following manner.

(Evaluation of Siloxane Resistance)

Each of the compounds (lubricants) synthesized in the later-described manner, in an amount of 0.15 g, was dissolved in 150 g of Vertrel-XF (registered trademark) available from DuPont, and then stirred for 1 hour to give a lubricant solution. Then, Graphite powder <20 µm available from Aldrich in an amount of 1.0 g was added to the obtained lubricant solution, and then stirred for another 1 hour. The obtained solution was subjected to filtration using a membrane filter to obtain graphite having the lubricant adsorbed thereon. The graphite having the lubricant adsorbed thereon was dried at room temperature for 15 hours, and then 0.1 g of the graphite having the lubricant adsorbed thereon was weighed into a Petri dish. The Petri dish containing the graphite having the lubricant adsorbed thereon and a vial containing octamethylcyclotetrasiloxane (0.5 g) available from TOKYO CHEMICAL INDUSTRY CO., LTD. were placed in a container and hermetically closed, and the graphite having the lubricant adsorbed thereon was exposed to octamethylcyclotetrasiloxane (hereinafter referred to as D4 in this specification) at room temperature (25° C.) for 24 hours. The Petri dish was removed from the container, methanol (2.2 g) was added to the Petri dish, and thereby D4 attached to the graphite was extracted. The extracted D4 was subjected to filtration using a membrane filter, and then the obtained filtrate was analyzed with use of a gas chromatograph (available from HEWLETT PACKARD, Product No. HP6890) and thereby the amount of D4 attached to the graphite was measured. The graphite having the lubricant adsorbed thereon was heated to 550° C. with use of a thermogravimetric analyzer (available from EXTER, TG/DTA) in a nitrogen atmosphere at a temperature increase rate of 2° C./min., and thereby the percentage by weight of the lubricant adsorbed on the graphite relative to the graphite (the amount of lubricant adsorbed on graphite) was determined.

(Evaluation of Heat Resistance)

The heat resistance of lubricants was evaluated with use of a thermogravimetric analyzer (available from Yamato Scientific Co., Ltd., TG/DTA). Each of the compounds (lubricants) synthesized in the later-describe manner, in an amount of 5 mg, was placed in a platinum container, heated to 550° C. in a nitrogen atmosphere at a temperature increase rate of 2° C./min., the temperature at which the weight of the compound decreased by 10% (such a temperature is referred to as 10% thermal weight loss temperature) was measured, and the heat resistance of the lubricant was evaluated.

Example 1

Compounds 1A to 1C, which are fluoropolyether compounds having a structure represented by Formula (3) below, were synthesized.

HOCH$_2$CH(OH)CH$_2$OCH$_2$CF$_2$CF$_2$O(CF$_2$CF$_2$CF$_2$O)$_m$
CF$_2$CF$_2$CH$_2$—(OCH$_2$CH(OH)CH$_2$CH$_2$—
CH$_2$CH$_2$CH(OH)CH$_2$O—CH$_2$CF$_2$CF$_2$O
(CF$_2$CF$_2$CF$_2$O)$_n$CF$_2$CF$_2$CH$_2$)$_p$—OCH$_2$CH(OH)
CH$_2$OH  (3)

Example 1A

In an argon atmosphere, a mixture of t-butyl alcohol (68.6 g), 160 g of a perfluoropolyether represented by HO—CH$_2$CF$_2$CF$_2$O(CF$_2$CF$_2$CF$_2$O)$_n$CF$_2$CF$_2$CH$_2$—OH (number average molecular weight: 756), potassium t-butoxide (2.1 g), and glycidol (13.3 g) was stirred at 70° C. for 22 hours. Then, the obtained mixture was washed with water, dehydrated, and then purified by silica gel column chromatography, thereby giving 105 g of a mixture of the perfluoropolyether (source material) and another perfluoropolyether having one hydroxyl group at one terminal thereof and having two hydroxyl groups (which result from reaction with glycidol) at the other terminal thereof (number average molecular weight of the mixture: 754). This mixture (25 g) was dissolved in meta-xylene hexafluoride (25 g), and sodium hydroxide (2.3 g) and 1,7-octadienediepoxide (2.3 g) were added thereto, followed by stirring at 70° C. for 20 hours. The obtained mixture was washed with water, dehydrated, and purified by distillation, thereby giving 9.7 g of Compound 1A.

Compound 1A was a colorless transparent liquid, and the density of Compound 1A was 1.75 g/cm$^3$ at 20° C. Compound 1A was identified by NMR. The results of the NMR are as follows.

$^{19}$F-NMR (solvent: none, reference material: —OCF$_2$CF$_2$CF$_2$O— in the product [−129.7 ppm])

δ=−129.7ppm [33F, —OCF$_2$CF$_2$CF$_2$O—]

δ=−83.7 ppm [67F, —OCF$_2$CF$_2$CF$_2$O—]

δ=−124.2 ppm [18F, —OCF$_2$CF$_2$CH$_2$OCH$_2$CH(OH)CH$_2$CH$_2$CH$_2$CH$_2$CH(OH)CH$_2$—, —OCF$_2$CF$_2$CH$_2$OCH$_2$CH(OH)CH$_2$OH]

δ=−86.5 ppm [18F, —OCF$_2$CF$_2$CH$_2$OCH$_2$CH(OH)CH$_2$CH$_2$CH$_2$CH(OH)CH$_2$—, —OCF$_2$CF$_2$CH$_2$OCH$_2$CH(OH)CH$_2$OH]

$^1$H-NMR (solvent: none, standard substance: D$_2$O)

δ=2.5 to 4.5 ppm [59H, HOCH$_2$CH(OH)CH$_2$OCH$_2$CF$_2$CF$_2$O(CF$_2$CF$_2$CF$_2$O)$_m$CF$_2$CF$_2$CH$_2$—(OCH$_2$CH(OH)CH$_2$CH$_2$CH$_2$CH$_2$CH(OH)CH$_2$O—CH$_2$CF$_2$CF$_2$O(CF$_2$CF$_2$CF$_2$O)$_n$CF$_2$CF$_2$CH$_2$)$_p$—OCH$_2$CH(OH)CH$_2$OH]

δ=1.1 ppm [27H, HOCH$_2$CH(OH)CH$_2$OCH$_2$CF$_2$CF$_2$O(CF$_2$CF$_2$CF$_2$O)$_m$CF$_2$CF$_2$CH$_2$—(OCH$_2$CH(OH)CH$_2$CH$_2$CH$_2$CH(OH)CH$_2$O—CH$_2$CF$_2$CF$_2$O(CF$_2$CF$_2$CF$_2$O)$_n$CF$_2$CF$_2$CH$_2$)$_p$—OCH$_2$CH(OH)CH$_2$OH]

The results of $^{19}$F-NMR and $^1$H-NMR demonstrate that Compound 1A is a compound represented by Formula (3) where n=m=3.8 and p=3.4.

Example 1B

Compound 1B was synthesized in the same manner as described in Example 1A, except that 6.7 g of glycidol was used and 4.6 g of 1,7-octadienediepoxide was used in the synthesis method described in Example 1A.

Compound 1B was a colorless transparent liquid, and the density of Compound 1B was 1.76 g/cm$^3$ at 20° C. Compound 1B was identified by NMR. The results of the NMR are as follows.

$^{19}$F-NMR (solvent: none, reference material: —OCF$_2$CF$_2$CF$_2$O— in the product [−129.7 ppm])

δ=−129.7 ppm [45F, —OCF$_2$CF$_2$CF$_2$O—]

δ=−83.7 ppm [91F, —OCF$_2$CF$_2$CF$_2$O—]

δ=−124.2 ppm [25F, —OCF$_2$CF$_2$CH$_2$OCH$_2$ CH(OH)CH$_2$CH$_2$CH$_2$CH$_2$CH(OH)CH$_2$—, —OCF$_2$CF$_2$CH$_2$OCH$_2$CH(OH)CH$_2$OH]

δ=−86.5 ppm [25F, —OCF$_2$CF$_2$CH$_2$OCH$_2$CH(OH)CH$_2$CH$_2$CH$_2$CH$_2$CH(OH)CH$_2$—, —OCF$_2$CF$_2$CH$_2$OCH$_2$CH(OH)CH$_2$OH]

$^1$H-NMR (solvent: none, standard substance: D$_2$O)

δ=2.5 to 4.5 ppm [82H, HOCH$_2$CH(OH)CH$_2$OCH$_2$CF$_2$CF$_2$O(CF$_2$CF$_2$CF$_2$O)$_m$CF$_2$CF$_2$CH$_2$—(OCH$_2$CH(OH)CH$_2$CH$_2$CH$_2$CH$_2$CH(OH)CH$_2$O—CH$_2$CF$_2$CF$_2$O(CF$_2$CF$_2$CF$_2$O)$_n$CF$_2$CF$_2$CH$_2$)$_p$—OCH$_2$CH(OH)CH$_2$OH]

δ=1.1 ppm [42H, HOCH$_2$CH(OH)CH$_2$OCH$_2$CF$_2$CF$_2$O(CF$_2$CF$_2$CF$_2$O)$_m$CF$_2$CF$_2$CH$_2$—(OCH$_2$CH(OH)CH$_2$CH$_2$CH$_2$CH(OH)CH$_2$O—CH$_2$CF$_2$CF$_2$O(CF$_2$CF$_2$CF$_2$O)$_n$CF$_2$CF$_2$CH$_2$)$_p$—OCH$_2$CH(OH)CH$_2$OH]

The results of $^{19}$F-NMR and $^1$H-NMR demonstrate that Compound 1B is a compound represented by Formula (3) where n=m=3.6 and p=5.3.

Example 1C

Compound 1C was synthesized in the same manner as described in Example 1A, except that 3.5 g of glycidol was used and 9.2 g of 1,7-octadienediepoxide was used in the synthesis method described in Example 1A.

Compound 1C was a colorless transparent liquid, and the density of Compound 1C was 1.77 g/cm$^3$ at 20° C. Compound 1C was identified by NMR. The results of the NMR are as follows.

$^{19}$F-NMR (solvent: none, reference material: —OCF$_2$CF$_2$CF$_2$O— in the product [−129.7 ppm])

δ=−129.7 ppm [75F, —OCF$_2$CF$_2$CF$_2$O—]

δ=−83.7 ppm [151F, —OCF$_2$CF$_2$CF$_2$O—]

δ=−124.2 ppm [41F, —OCF$_2$CF$_2$CH$_2$OCH$_2$CH(OH)CH$_2$CH$_2$CH$_2$CH$_2$CH(OH)CH$_2$—, —OCF$_2$CF$_2$CH$_2$OCH$_2$CH(OH)CH$_2$OH]

δ=−86.5 ppm [41F, —OCF$_2$CF$_2$CH$_2$OCH$_2$CH(OH)CH$_2$CH$_2$CH$_2$CH(OH)CH$_2$—, —OCF$_2$CF$_2$CH$_2$OCH$_2$CH(OH) CH$_2$OH]

$^1$H-NMR (solvent: none, standard substance: D$_2$O)

δ=2.5 to 4.5 ppm [128H, HOCH$_2$CH(OH)CH$_2$OCH$_2$CF$_2$CF$_2$O(CF$_2$CF$_2$CF$_2$O)$_m$CF$_2$CF$_2$CH$_2$—(OCH$_2$CH(OH)CH$_2$CH$_2$CH$_2$CH(OH)CH$_2$O—CH$_2$CF$_2$CF$_2$O(CF$_2$CF$_2$CF$_2$O)$_n$CF$_2$CF$_2$CH$_2$)$_p$—OCH$_2$CH(OH)CH$_2$OH]

δ=1.1 ppm [74H, HOCH$_2$CH(OH)CH$_2$OCH$_2$CF$_2$CF$_2$O(CF$_2$CF$_2$CF$_2$O)$_m$CF$_2$CF$_2$CH$_2$—(OCH$_2$CH(OH)CH$_2$CH$_2$CH$_2$CH(OH)CH$_2$O—CH$_2$CF$_2$CF$_2$O(CF$_2$CF$_2$CF$_2$O)$_n$CF$_2$CF$_2$CH$_2$)$_p$—OCH$_2$CH(OH)CH$_2$OH]

The results of $^{19}$F-NMR and $^1$H-NMR demonstrate that Compound 1C is a compound represented by Formula (3) where n=m=3.7 and p=9.2.

Example 2

Compounds 2A to 2C, which are fluoropolyether compounds having a structure represented by Formula (4) below, were synthesized.

$$\text{HOCH}_2\text{CH(OH)CH}_2\text{OCH}_2\text{CF}_2\text{CF}_2\text{O(CF}_2\text{CF}_2\text{CF}_2\text{O)}_m \\ \text{CF}_2\text{CF}_2\text{CH}_2(\text{OCH}_2\text{CH(OH)CH}_2\text{OC}_6\text{H}_4\text{—} \\ \text{OCH}_2\text{CH(OH)CH}_2\text{O—CH}_2\text{CF}_2\text{CF}_2\text{O} \\ (\text{CF}_2\text{CF}_2\text{CF}_2\text{O})_n\text{CF}_2\text{CF}_2\text{CH}_2)_p\text{—OCH}_2\text{CH(OH)} \\ \text{CH}_2\text{OH} \quad (4)$$

Example 2A

In an argon atmosphere, a mixture of t-butyl alcohol (68.6 g), 150 g of a perfluoropolyether represented by HO—CH$_2$CF$_2$CF$_2$O(CF$_2$CF$_2$CF$_2$O)$_n$CF$_2$CF$_2$CH$_2$—OH (number average molecular weight: 838), potassium t-butoxide (1.8 g), and glycidol (11.3 g) was stirred at 70° C. for 19 hours. The obtained mixture was washed with water, dehydrated, and then purified by silica gel column chromatography, thereby giving 105 g of a mixture of the perfluoropolyether (source material) and another perfluoropolyether having one hydroxyl group at one terminal thereof and having two hydroxyl groups (which result from reaction with glycidol) at the other terminal thereof (number average molecular weight of the mixture: 754). This mixture (90 g) was dissolved in t-butyl alcohol (39 g), and potassium t-butoxide (1.7 g) and resorcinol diglycidyl ether (15.4 g) were added thereto, followed by stirring at 70° C. for 17 hours. Then, the obtained mixture was washed with water, dehydrated, and purified by distillation, thereby giving 53 g of Compound 2A.

Compound 2A was a colorless transparent liquid, and the density of Compound 2A was 1.72 g/cm$^3$ at 20° C. Compound 2A was identified by NMR. The results of the NMR are as follows.

$^{19}$F-NMR (solvent: none, reference material: —OCF$_2$CF$_2$CF$_2$O— in the product [−129.7 ppm])

δ=−129.7 ppm [38F, —OCF$_2$CF$_2$CF$_2$O—]

δ=−83.7 ppm [76F, —OCF$_2$CF$_2$CF$_2$O—]

δ=−124.2 ppm [17F, —OCF$_2$CF$_2$CH$_2$OCH$_2$CH(OH)CH$_2$OC$_6$H$_4$OCH$_2$CH(OH)CH$_2$—, —OCF$_2$CF$_2$CH$_2$OCH$_2$CH(OH)CH$_2$OH]

δ=−86.5 ppm [17F, —OCF$_2$CF$_2$CH$_2$OCH$_2$CH(OH)CH$_2$OC$_6$H$_4$OCH$_2$CH(OH)CH$_2$—, —OCF$_2$CF$_2$CH$_2$OCH$_2$CH(OH)CH$_2$OH]

$^1$H-NMR (solvent: none, standard substance: D$_2$O)

δ=2.5 to 4.5 ppm [71H, HOCH$_2$CH(OH)CH$_2$OCH$_2$CF$_2$CF$_2$O(CF$_2$CF$_2$CF$_2$O)$_m$CF$_2$CF$_2$CH$_2$—(OCH$_2$CH(OH)CH$_2$OC$_6$H$_4$OCH$_2$CH(OH)CH$_2$O—CH$_2$CF$_2$CF$_2$O(CF$_2$CF$_2$CF$_2$O)$_n$CF$_2$CF$_2$CH$_2$)$_p$—OCH$_2$CH(OH)CH$_2$OH]

δ=6.0 to 7.5 ppm [13H, HOCH$_2$CH(OH)CH$_2$OCH$_2$CF$_2$CF$_2$O(CF$_2$CF$_2$CF$_2$O)$_m$CF$_2$CF$_2$CH$_2$—(OCH$_2$CH(OH)CH$_2$OC$_6$H$_4$OCH$_2$CH(OH)CH$_2$O—CH$_2$CF$_2$CF$_2$O(CF$_2$CF$_2$CF$_2$O)$_n$CF$_2$CF$_2$CH$_2$)$_p$—OCH$_2$CH(OH)CH$_2$OH]

The results of $^{19}$F-NMR and $^1$H-NMR demonstrate that Compound 2A is a compound represented by Formula (4) where n=m=4.4 and p=3.3.

Example 2B

Compound 2B was synthesized in the same manner as described in Example 2A, except that 6.7 g of glycidol was used and 30.8 g of resorcinol diglycidyl ether was used in the synthesis method described in Example 2A.

Compound 2B was a colorless transparent liquid, and the density of Compound 2B was 1.77 g/cm$^3$ at 20° C. Compound 2B was identified by NMR. The results of the NMR are as follows.

$^{19}$F-NMR (solvent: none, reference material: —OCF$_2$CF$_2$CF$_2$O— in the product [−129.7 ppm])

δ=−129.7 ppm [56F, —OCF$_2$CF$_2$CF$_2$O—]

δ=−83.7 ppm [112F, —OCF$_2$CF$_2$CF$_2$O—]

δ=−124.2 ppm [25F, —OCF$_2$CF$_2$CH$_2$OCH$_2$ CH(OH)CH$_2$OC$_6$H$_4$OCH$_2$CH(OH)CH$_2$—, —OCF$_2$CF$_2$CH$_2$OCH$_2$CH(OH)CH$_2$OH]

δ=−86.5 ppm [25F, —OCF$_2$CF$_2$CH$_2$OCH$_2$CH(OH)CH$_2$OC$_6$H$_4$OCH$_2$CH(OH)CH$_2$—, —OCF$_2$CF$_2$CH$_2$OCH$_2$CH(OH) CH$_2$OH]

$^1$H-NMR (solvent: none, standard substance: D$_2$O)

δ=2.5 to 4.5 ppm [101H, HOCH$_2$CH(OH)CH$_2$OCH$_2$CF$_2$CF$_2$O(CF$_2$CF$_2$CF$_2$O)$_m$CF$_2$CF$_2$CH$_2$—(OCH$_2$CH(OH)CH$_2$OC$_6$H$_4$OCH$_2$CH(OH)CH$_2$O—CH$_2$CF$_2$CF$_2$O(CF$_2$CF$_2$CF$_2$O)$_n$CF$_2$CF$_2$CH$_2$)$_p$—OCH$_2$CH(OH)CH$_2$OH]

δ=6.0 to 7.5 ppm [21H, HOCH$_2$CH(OH)CH$_2$OCH$_2$CF$_2$CF$_2$O(CF$_2$CF$_2$CF$_2$O)$_m$CF$_2$CF$_2$CH$_2$—(OCH$_2$CH(OH)CH$_2$OC$_6$H$_4$OCH$_2$CH(OH)CH$_2$O—CH$_2$CF$_2$CF$_2$O(CF$_2$CF$_2$CF$_2$O)$_n$CF$_2$CF$_2$CH$_2$)$_p$—OCH$_2$CH(OH)CH$_2$OH]

The results of $^{19}$F-NMR and $^1$H-NMR demonstrate that Compound 2B is a compound represented by Formula (4) where n=m=4.5 and p=5.2.

Example 2C

Compound 2C was synthesized in the same manner as described in Example 2A, except that 3.5 g of glycidol was used and 61.6 g of resorcinol diglycidyl ether was used in the synthesis method described in Example 2A.

Compound 2C was a colorless transparent liquid, and the density of Compound 2C was 1.77 g/cm$^3$ at 20° C. Compound 2C was identified by NMR. The results of the NMR are as follows.

$^{19}$F-NMR (solvent: none, reference material: —OCF$_2$CF$_2$CF$_2$O— in the product [−129.7 ppm])

δ=−129.7 ppm [91F, —OCF$_2$CF$_2$CF$_2$O—]

δ=−83.7 ppm [182F, —OCF$_2$CF$_2$CF$_2$O—]

δ=−124.2 ppm [40F, —OCF$_2$CF$_2$CH$_2$OCH$_2$CH(OH)CH$_2$OC$_6$H$_4$OCH$_2$CH(OH)CH$_2$—, —OCF$_2$CF$_2$CH$_2$OCH$_2$CH(OH)CH$_2$OH]

δ=−86.5 ppm [40F, —OCF$_2$CF$_2$CH$_2$OCH$_2$CH(OH)CH$_2$OC$_6$H$_4$OCH$_2$CH(OH)CH$_2$—, —OCF$_2$CF$_2$CH$_2$OCH$_2$CH(OH)CH$_2$OH]

$^1$H-NMR (solvent: none, standard substance: D$_2$O)

δ=2.5 to 4.5 ppm [164H, HOCH$_2$CH(OH)CH$_2$OCH$_2$CF$_2$CF$_2$O(CF$_2$CF$_2$CF$_2$O)$_m$CF$_2$CF$_2$CH$_2$—(OCH$_2$CH(OH)CH$_2$OC$_6$H$_4$OCH$_2$CH(OH)CH$_2$O—CH$_2$CF$_2$CF$_2$O(CF$_2$CF$_2$CF$_2$O)$_n$CF$_2$CF$_2$CH$_2$)$_p$—OCH$_2$CH(OH)CH$_2$OH]

δ=6.0 to 7.5 ppm [36H, HOCH$_2$CH(OH)CH$_2$OCH$_2$CF$_2$CF$_2$ O(CF$_2$CF$_2$CF$_2$O)$_m$CF$_2$CF$_2$CH$_2$—(OCH$_2$CH(OH)CH$_2$OC$_6$H$_4$OCH$_2$CH(OH)CH$_2$O—CH$_2$CF$_2$CF$_2$O(CF$_2$CF$_2$CF$_2$O)$_n$CF$_2$CF$_2$CH$_2$)$_p$—OCH$_2$CH(OH)CH$_2$OH]

The results of $^{19}$F-NMR and $^1$H-NMR demonstrate that Compound 2C is a compound represented by Formula (4) where n=m=4.5 and p=9.1.

Example 3

Compounds 3A to 3C, which are fluoropolyether compounds having a structure represented by Formula (5) below, were synthesized.

CH$_3$OC$_6$H$_4$OCH$_2$CH(OH)CH$_2$OCH$_2$CF$_2$CF$_2$O
(CF$_2$CF$_2$CF$_2$O)$_m$CF$_2$CF$_2$CH$_2$(OCH$_2$CH(OH)—
CH$_2$CH$_2$CH$_2$CH$_2$CH(OH)CH$_2$O—
CH$_2$CF$_2$CF$_2$O(CF$_2$CF$_2$CF$_2$O)$_n$CF$_2$CF$_2$CH$_2$)$_p$—
OCH$_2$CH(OH)—CH$_2$OC$_6$H$_4$OCH$_3$ (5)

Example 3A

In an argon atmosphere, 160 g of a perfluoropolyether represented by HO—CH$_2$CF$_2$CF$_2$O(CF$_2$CF$_2$CF$_2$O)$_n$CF$_2$CF$_2$CH$_2$—OH (number average molecular weight: 756) was dissolved in meta-xylene hexafluoride (160 g), then sodium hydroxide (2.3 g) and 1,7-octadienediepoxide (26 g) were added, and stirred at 70° C. for 20 hours. The obtained mixture was washed with water, dehydrated, and then purified by distillation, the obtained compound was dissolved in t-butyl alcohol (60 g), and potassium t-butoxide (0.5 g) and 4-methoxyphenyl glycidyl ether (17.6 g) were added thereto, followed by stirring at 70° C. for 19 hours. The obtained mixture was washed with water, dehydrated, and then purified by column chromatography, thereby giving 90 g of Compound 3A.

Compound 3A was a colorless transparent liquid, and the density of Compound 3A was 1.77 g/cm$^3$ at 20° C. Compound 3A was identified by NMR. The results of the NMR are as follows.

$^{19}$F-NMR (solvent: none, reference material: —OCF$_2$CF$_2$CF$_2$O— in the product [−129.7 ppm])

δ=−129.7 ppm [32F, —OCF$_2$CF$_2$CF$_2$O—]

δ=−83.7 ppm [63F, —OCF$_2$CF$_2$CF$_2$O—]

δ=−124.2 ppm [18F, —OCF$_2$CF$_2$CH$_2$OCH$_2$ CH(OH) CH$_2$CH$_2$CH$_2$CH$_2$CH(OH)CH$_2$—, —OCF$_2$CF$_2$CH$_2$ OCH$_2$CH(OH)CH$_2$OH]

δ=−86.5 ppm [18F, —OCF$_2$CF$_2$CH$_2$OCH$_2$CH(OH)CH$_2$ CH$_2$CH$_2$CH$_2$CH(OH)CH$_2$—, —OCF$_2$CF$_2$CH$_2$OCH$_2$ CH(OH)CH$_2$OH]

$^1$H-NMR (solvent: none, standard substance: D$_2$O)

δ=2.5 to 4.5 ppm [64H, CH$_3$OC$_6$H$_4$OCH$_2$CH(OH)C H$_2$OCH$_2$CF$_2$CF$_2$O(CF$_2$CF$_2$CF$_2$O)$_m$CF$_2$CF$_2$CH$_2$—(OCH$_2$C H(OH)CH$_2$CH$_2$CH$_2$CH$_2$CH(OH)CH$_2$O—CH$_2$CF$_2$CF$_2$ O(CF$_2$CF$_2$CF$_2$O)$_n$CF$_2$CF$_2$CH$_2$)$_p$—OCH$_2$CH(OH)C H$_2$OC$_6$H$_4$OCH$_3$]

δ=1.1 ppm [28H, CH$_3$OC$_6$H$_4$OCH$_2$CH(OH)CH$_2$OCH$_2$ CF$_2$ CF$_2$O(CF$_2$CF$_2$CF$_2$O)$_m$CF$_2$CF$_2$CH$_2$—(OCH$_2$CH(OH)C H$_2$CH$_2$CH$_2$CH$_2$CH(OH)CH$_2$O—CH$_2$CF$_2$CF$_2$O (CF$_2$CF$_2$ CF$_2$O)$_n$CF$_2$CF$_2$CH$_2$)$_p$—OCH$_2$CH(OH)CH$_2$OC$_6$H$_4$OCH$_3$]

δ=6.0 to 7.5 ppm [8H, CH$_3$OC$_6$H$_4$OCH$_2$CH(OH) CH$_2$OCH$_2$CF$_2$CF$_2$O(CF$_2$CF$_2$CF$_2$O)$_m$CF$_2$CF$_2$CH$_2$— (OCH$_2$CH(OH)CH$_2$CH$_2$CH$_2$CH$_2$CH(OH)CH$_2$O— CH$_2$CF$_2$CF$_2$O(CF$_2$CF$_2$CF$_2$O)$_n$CF$_2$CF$_2$CH$_2$)$_p$—OCH$_2$CH (OH)CH$_2$OC$_6$H$_4$OCH$_3$]

The results of $^{19}$F-NMR and $^1$H-NMR demonstrate that Compound 3A is a compound represented by Formula (5) where n=m=3.5 and p=3.5.

Example 3B

In an argon atmosphere, 160 g of a perfluoropolyether represented by HO—CH$_2$CF$_2$CF$_2$O(CF$_2$CF$_2$CF$_2$O)$_n$CF$_2$ CF$_2$ CH$_2$—OH (number average molecular weight: 756) was dissolved in meta-xylene hexafluoride (160 g), then sodium hydroxide (2.3 g) and 1,7-octadienediepoxide (26 g) were added, and stirred at 70° C. for 20 hours. Then, 1,7-octadienediepoxide (13 g) was further added and stirred at 70° C. for 20 hours. The obtained mixture was washed with water, dehydrated, and then the same process as described in Example 3A was carried out to obtain Compound 3B.

Compound 3B was a colorless transparent liquid, and the density of Compound 3B was 1.78 g/cm$^3$ at 20° C. Compound 3B was identified by NMR. The results of the NMR are as follows.

$^{19}$F-NMR (solvent: none, reference material: —OCF$_2$C F$_2$CF$_2$O— in the product [−129.7 ppm])

δ=−129.7 ppm [42F, —OCF$_2$CF$_2$CF$_2$O—]

δ=−83.7 ppm [84F, —OCF$_2$CF$_2$CF$_2$O—],

δ=−124.2 ppm [24F, —OCF$_2$CF$_2$CH$_2$OCH$_2$ CH(OH) CH$_2$CH$_2$CH$_2$CH$_2$CH(OH)CH$_2$—, —OCF$_2$CF$_2$CH$_2$ OCH$_2$CH(OH)CH$_2$OH]

δ=−86.5 ppm [24F, —OCF$_2$CF$_2$CH$_2$OCH$_2$CH(OH)CH$_2$ CH$_2$CH$_2$CH$_2$CH(OH)CH$_2$—, —OCF$_2$CF$_2$CH$_2$OCH$_2$ CH(OH)CH$_2$OH]

$^1$H-NMR (solvent: none, standard substance: D$_2$O)

δ=2.5 to 4.5 ppm [82H, CH$_3$OC$_6$H$_4$OCH$_2$CH(OH)C H$_2$OCH$_2$CF$_2$CF$_2$O(CF$_2$CF$_2$CF$_2$O)$_m$CF$_2$CF$_2$CH$_2$—(OCH$_2$C H(OH)CH$_2$CH$_2$CH$_2$CH$_2$CH(OH)CH$_2$O—CH$_2$CF$_2$CF$_2$ O(CF$_2$CF$_2$CF$_2$O)$_n$CF$_2$CF$_2$CH$_2$)$_p$—OCH$_2$CH(OH)C H$_2$OC$_6$H$_4$OCH$_3$ ]

δ=1.1 ppm [40H, CH$_3$OC$_6$H$_4$OCH$_2$CH(OH)CH$_2$OCH$_2$ CF$_2$CF$_2$O(CF$_2$CF$_2$CF$_2$O)$_m$CF$_2$CF$_2$CH$_2$—(OCH$_2$CH(OH)C H$_2$CH$_2$CH$_2$CH$_2$CH(OH)CH$_2$O—CH$_2$CF$_2$CF$_2$O(CF$_2$CF$_2$ CF$_2$O)$_n$CF$_2$CF$_2$CH$_2$)$_p$—OCH$_2$CH(OH)CH$_2$OC$_6$H$_4$OCH$_3$]

δ=6.0 to 7.5 ppm [8H, CH$_3$OC$_6$ H$_4$OCH$_2$CH(OH)CH$_2$OCH$_2$ CF$_2$CF$_2$O(CF$_2$CF$_2$CF$_2$O)$_m$ CF$_2$CF$_2$CH$_2$—(OCH$_2$CH(OH)CH$_2$CH$_2$CH$_2$CH$_2$CH(OH) CH$_2$O—CH$_2$CF$_2$CF$_2$O(CF$_2$CF$_2$CF$_2$O)$_n$CF$_2$CF$_2$CH$_2$)$_p$— OCH$_2$CH(OH)CH$_2$OC$_6$H$_4$OCH$_3$]

The results of $^{19}$F-NMR and $^1$H-NMR demonstrate that Compound 3B is a compound represented by Formula (5) where n=m=3.5 and p=5.0.

Example 3C

In an argon atmosphere, 160 g of a perfluoropolyether represented by HO—CH$_2$CF$_2$CF$_2$O(CF$_2$CF$_2$CF$_2$O)$_n$CF$_2$ CF$_2$CH$_2$—OH (number average molecular weight: 756) was dissolved in meta-xylene hexafluoride (160 g), then sodium hydroxide (2.3 g) and 1,7-octadienediepoxide (26 g) were added, and stirred at 70° C. for 20 hours. Then, 1,7-octadienediepoxide (13 g) was further added and stirred at 70° C. for 20 hours. Then, 1,7-octadienediepoxide (13 g) was further added and stirred at 70° C. for 20 hours. The obtained mixture was washed with water, dehydrated, and then the same process as described in Example 3A was carried out to obtain Compound 3C.

Compound 3C was a colorless transparent liquid, and the density of Compound 3C was 1.79 g/cm$^3$ at 20° C. Compound 3C was identified by NMR. The results of the NMR are as follows.

$^{19}$F-NMR (solvent: none, reference material: —OCF$_2$C F$_2$CF$_2$O— in the product [−129.7 ppm])

δ=−129.7 ppm [70F, —OCF$_2$CF$_2$CF$_2$O—]

δ=−83.7 ppm [140F, —OCF$_2$CF$_2$CF$_2$O—]

δ=−124.2 ppm [40F, —OCF$_2$CF$_2$CH$_2$OCH$_2$ CH(OH) CH$_2$CH$_2$CH$_2$CH$_2$CH(OH)CH$_2$—, —OCF$_2$CF$_2$CH$_2$OCH$_2$ CH(OH)CH$_2$OH]

δ=−86.5 ppm [40F, —OCF$_2$CF$_2$CH$_2$OCH$_2$CH(OH)CH$_2$ CH$_2$CH$_2$CH$_2$CH(OH)CH$_2$—, —OCF$_2$CF$_2$CH$_2$OCH$_2$CH (OH)CH$_2$OH]

$^1$H-NMR (solvent: none, standard substance: D$_2$O)

δ=2.5 to 4.5 ppm [130H, CH$_3$OC$_6$H$_4$OCH$_2$CH(OH)C H$_2$OCH$_2$CF$_2$CF$_2$O(CF$_2$CF$_2$CF$_2$O)$_m$CF$_2$CF$_2$CH$_2$—(OCH$_2$ CH(OH)CH$_2$CH$_2$CH$_2$CH$_2$CH(OH)CH$_2$O—CH$_2$CF$_2$ CF$_2$O (CF$_2$CF$_2$CF$_2$O)$_n$CF$_2$CF$_2$CH$_2$)$_p$—OCH$_2$CH(OH)C H$_2$OC$_6$H$_4$OCH$_3$]

δ=1.1 ppm [72H, CH$_3$OC$_6$H$_4$OCH$_2$CH(OH)CH$_2$OCH$_2$ CF$_2$CF$_2$O(CF$_2$CF$_2$CF$_2$O)$_m$CF$_2$CF$_2$CH$_2$—(OCH$_2$CH(OH)C H$_2$CH$_2$CH$_2$CH$_2$CH(OH)CH$_2$O—CH$_2$CF$_2$CF$_2$O(CF$_2$ CF$_2$CF$_2$ O)$_n$CF$_2$CF$_2$CH$_2$)$_p$—OCH$_2$CH(OH)CH$_2$OC$_6$H$_4$ OCH$_3$]

δ=6.0 to 7.5 ppm [8H, CH$_3$OC$_6$H$_4$OCH$_2$ CH(OH) CH$_2$OCH$_2$CF$_2$ CF$_2$(CF$_2$CF$_2$CF$_2$O)$_m$CF$_2$CF$_2$CH$_2$—(OCH$_2$ CH(OH)CH$_2$CH$_2$CH$_2$CH$_2$CH(OH)CH$_2$O—CH$_2$CF$_2$CF$_2$O (CF$_2$CF$_2$CF$_2$O)$_n$CF$_2$CF$_2$CH$_2$)$_p$—OCH$_2$CH(OH)CH$_2$OC$_6$ H$_4$OCH$_3$]

The results of $^{19}$F-NMR and $^1$H-NMR demonstrate that Compound 3C is a compound represented by Formula (5) where n=m=3.5 and p=9.0.

Example 4

Compounds 4A to 4C, which are fluoropolyether compounds having a structure represented by Formula (6) below, were synthesized.

CH$_3$OC$_6$H$_4$OCH$_2$CH(OH)CH$_2$OCH$_2$CF$_2$CF$_2$O
(CF$_2$CF$_2$CF$_2$O)$_m$CF$_2$CF$_2$CH$_2$(OCH$_2$CH$_2$CH
(OH)—CH$_2$OC$_6$H$_4$OCH$_2$CH(OH)CH$_2$O—
CH$_2$CF$_2$CF$_2$O(CF$_2$CF$_2$CF$_2$O)$_n$CF$_2$CF$_2$CH$_2$)$_p$—
OCH$_2$CH(OH)—CH$_2$OC$_6$H$_4$OCH$_3$ (6)

Example 4A

In an argon atmosphere, 150 g of a perfluoropolyether represented by HO—CH$_2$CF$_2$CF$_2$O(CF$_2$CF$_2$CF$_2$O)$_n$ CF$_2$CF$_2$CH$_2$—OH (number average molecular weight:

838) was dissolved in meta-xylene hexafluoride (150 g), sodium hydroxide (2.3 g) and resorcinol diglycidyl ether (22 g) were added, and stirred at 70° C. for 20 hours. Then, the obtained mixture was washed with water, dehydrated, and then purified by column chromatography, the obtained compound was dissolved in t-butyl alcohol (60 g), and potassium t-butoxide (0.5 g) and 4-methoxyphenyl glycidyl ether (17.6 g) were added thereto, followed by stirring at 70° C. for 20 hours. The obtained mixture was washed with water, dehydrated, and then purified by column chromatography, thereby giving 78 g of Compound 4A.

Compound 4A was a colorless transparent liquid, and the density of Compound 4A was 1.80 g/cm$^3$ at 20° C. Compound 4A was identified by NMR. The results of the NMR are as follows.

$^{19}$F-NMR (solvent: none, reference material: —OC$F_2$C$F_2$C$F_2$O— in the product [–129.7 ppm])

δ=–129.7 ppm [33F, —OCF$_2$C$F_2$CF$_2$O—]

δ=–83.7 ppm [66F, —OC$F_2$CF$_2$C$F_2$O—]

δ=–124.2 ppm [16F, —OC$F_2$CF$_2$CH$_2$OCH$_2$ CH(OH) CH$_2$OC$_6$H$_4$OCH$_2$CH(OH)CH$_2$—, —OC$F_2$CF$_2$CH$_2$OCH$_2$CH(OH)CH$_2$OH]

δ=–86.5 ppm [16F, —OCF$_2$C$F_2$CH$_2$OCH$_2$ CH(OH) CH$_2$OC$_6$H$_4$OCH$_2$CH(OH)CH$_2$—, —OCF$_2$C$F_2$CH$_2$OCH$_2$CH(OH)CH$_2$OH]

$^1$H-NMR (solvent: none, standard substance: D$_2$O)

δ=2.5 to 4.5 ppm [70H, C$H_3$OC$_6$H$_4$OCH$_2$C$H$(O$H$)C$H_2$OC$H_2$CF$_2$CF$_2$O(CF$_2$CF$_2$CF$_2$O)$_m$CF$_2$CF$_2$C$H_2$—(OC$H_2$C$H$(O$H$)C$H_2$OC$_6$H$_4$C$H_2$C$H$(O$H$)C$H_2$O—C$H_2$CF$_2$CF$_2$O(CF$_2$CF$_2$CF$_2$O)$_n$CF$_2$CF$_2$C$H_2$)$_p$—OC$H_2$C$H$(O$H$)C$H_2$OC$_6$H$_4$OC$H_3$]

δ=6.0 to 7.5 ppm [20H, CH$_3$OC$_6$$H_4$OCH$_2$ CH(OH) CH$_2$OCH$_2$CF$_2$CF$_2$(CF$_2$CF$_2$CF$_2$O)$_m$CF$_2$CF$_2$CH$_2$—(OCH$_2$CH(OH)CH$_2$OC$_6$$H_4$OCH$_2$CH(OH)CH$_2$O—CH$_2$CF$_2$ CF$_2$O (CF$_2$CF$_2$CF$_2$O)$_n$CF$_2$CF$_2$CH$_2$)$_p$—OCH$_2$CH(OH)CH$_2$OC$_6$$H_4$OCH$_3$]

The results of $^{19}$F-NMR and $^1$H-NMR demonstrate that Compound 4A is a compound represented by Formula (6) where n=m=4.1 and p=3.0.

Example 4B

In an argon atmosphere, 150 g of a perfluoropolyether represented by HO—CH$_2$CF$_2$CF$_2$O(CF$_2$CF$_2$CF$_2$O)$_n$CF$_2$CF$_2$CH$_2$—OH (number average molecular weight: 838) was dissolved in meta-xylene hexafluoride (150 g), sodium hydroxide (2.3 g) and resorcinol diglycidyl ether (22 g) were added, and stirred at 70° C. for 20 hours. Then, resorcinol diglycidyl ether (11 g) was further added and stirred at 70° C. for 20 hours. The obtained mixture was washed with water, dehydrated, and then the same process as described in Example 4A was carried out to obtain Compound 4B.

Compound 4B was a colorless transparent liquid, and the density of Compound 4B was 1.74 g/cm$^3$ at 20° C. Compound 4B was identified by NMR. The results of the NMR are as follows.

$^{19}$F-NMR (solvent: none, reference material: —OCF$_2$C$F_2$CF$_2$O— in the product [–129.7 ppm])

δ=–129.7 ppm [54F, —OCF$_2$C$F_2$CF$_2$O—]

δ=–83.7 ppm [108F, —OC$F_2$CF$_2$C$F_2$O—]

δ=–124.2 ppm [26F, —OC$F_2$CF$_2$CH$_2$ OCH$_2$CH(OH)CH$_2$OC$_6$H$_4$OCH$_2$CH(OH)CH$_2$—, —OC$F_2$CF$_2$CH$_2$OCH$_2$CH(OH)CH$_2$OH]

δ=–86.5 ppm [26F, —OCF$_2$C$F_2$CH$_2$OCH$_2$ CH(OH) CH$_2$OC$_6$H$_4$OCH$_2$CH(OH)CH$_2$—, —OCF$_2$C$F_2$CH$_2$OCH$_2$CH(OH)CH$_2$OH]

$^1$H-NMR (solvent: none, standard substance: D$_2$O)

δ=2.5 to 4.5 ppm [108H, C$H_3$OC$_6$H$_4$OC$H_2$C$H$(O$H$)C$H_2$OC$H_2$CF$_2$CF$_2$O(CF$_2$CF$_2$CF$_2$O)$_m$CF$_2$CF$_2$C$H_2$—(OC$H_2$C$H$(O$H$)C$H_2$OC$_6$H$_4$OC$H_2$C$H$(O$H$)C$H_2$O—C$H_2$CF$_2$CF$_2$O(CF$_2$CF$_2$CF$_2$O)$_n$CF$_2$CF$_2$C$H_2$)$_p$—OC$H_2$C$H$(O$H$)C$H_2$OC$_6$H$_4$OC$H_3$]

δ=6.0 to 7.5 ppm [30H, CH$_3$OC$_6$$H_4$OCH$_2$CH(OH)CH$_2$OCH$_2$CF$_2$CF$_2$O(CF$_2$CF$_2$CF$_2$O)$_m$CF$_2$CF$_2$CH$_2$—(OCH$_2$CH(OH)CH$_2$OC$_6$$H_4$OCH$_2$CH(OH)CH$_2$O—CH$_2$CF$_2$CF$_2$O(CF$_2$CF$_2$CF$_2$O)$_n$CF$_2$CF$_2$CH$_2$)$_p$—OCH$_2$CH(OH)CH$_2$OC$_6$$H_4$OCH$_3$]

The results of $^{19}$F-NMR and $^1$H-NMR demonstrate that Compound 4B is a compound represented by Formula (6) where n=m=4.2 and p=5.4.

Example 4C

In an argon atmosphere, 150 g of a perfluoropolyether represented by HO—CH$_2$CF$_2$CF$_2$O(CF$_2$CF$_2$CF$_2$O)$_n$CF$_2$CF$_2$CH$_2$—OH (number average molecular weight: 838) was dissolved in meta-xylene hexafluoride (150 g), sodium hydroxide (2.3 g) and resorcinol diglycidyl ether (22 g) were added, and stirred at 70° C. for 20 hours. Then, resorcinol diglycidyl ether (11 g) was further added and stirred at 70° C. for 20 hours. Then, resorcinol diglycidyl ether (11 g) was further added and stirred at 70° C. for 20 hours. The obtained mixture was washed with water, dehydrated, and then the same process as described in Example 4A was carried out to obtain Compound 4C.

Compound 4C was a colorless transparent liquid, and the density of Compound 4C was 1.74 g/cm$^3$ at 20° C. Compound 4C was identified by NMR. The results of the NMR are as follows.

$^{19}$F-NMR (solvent: none, reference material: —OCF$_2$C$F_2$CF$_2$O— in the product [–129.7 ppm])

δ=–129.7 ppm [87F, —OCF$_2$C$F_2$CF$_2$O—]

δ=–83.7 ppm [175F, —OC$F_2$CF$_2$C$F_2$O—]

δ=–124.2 ppm [42F, —OC$F_2$CF$_2$CH$_2$OCH$_2$CH(OH) CH$_2$OC$_6$H$_4$OCH$_2$CH(OH)CH$_2$—, —OC$F_2$CF$_2$CH$_2$OCH$_2$CH(OH)CH$_2$OH]

δ=–86.5 ppm [42F, —OCF$_2$C$F_2$CH$_2$OCH$_2$ CH(OH) CH$_2$OC$_6$H$_4$OCH$_2$CH(OH)CH$_2$—, —OCF$_2$C$F_2$CH$_2$OCH$_2$CH(OH)CH$_2$OH]

$^1$H-NMR (solvent: none, standard substance: D$_2$O)

δ=2.5 to 4.5 ppm [172H, C$H_3$OC$_6$H$_4$OC$H_2$C$H$(O$H$)C$H_2$OC$H_2$CF$_2$CF$_2$O(CF$_2$CF$_2$CF$_2$O)$_m$CF$_2$CF$_2$C$H_2$—(OC$H_2$C$H$(O$H$)C$H_2$OC$_6$H$_4$OC$H_2$C$H$(O$H$)C$H_2$O—C$H_2$CF$_2$ CF$_2$O (CF$_2$CF$_2$CF$_2$O)$_n$CF$_2$CF$_2$C$H_2$)$_p$—OC$H_2$C$H$(O$H$)C$H_2$OC$_6$H$_4$OC$H_3$]

δ=6.0 to 7.5 ppm [46H, CH$_3$OC$_6$$H_4$OCH$_2$CH(OH)CH$_2$OCH$_2$CF$_2$CF$_2$O(CF$_2$CF$_2$CF$_2$O)$_m$CF$_2$CF$_2$CH$_2$—(OCH$_2$CH(OH)CH$_2$OC$_6$$H_4$OCH$_2$CH(OH)CH$_2$O—CH$_2$CF$_2$CF$_2$O(CF$_2$CF$_2$CF$_2$O)$_n$CF$_2$CF$_2$CH$_2$)$_p$—OCH$_2$CH(OH)CH$_2$OC$_6$$H_4$OCH$_3$]

The results of $^{19}$F-NMR and $^1$H-NMR demonstrate that Compound 4C is a compound represented by Formula (6) where n=m=4.2 and p=9.4.

Comparative Example 1

Comparative Compound 1, which is a fluoropolyether compound having a structure represented by Formula (7) below, was synthesized.

HOCH$_2$CH(OH)CH$_2$OCH$_2$CF$_2$CF$_2$O(CF$_2$CF$_2$CF$_2$O)$_n$CF$_2$CF$_2$CH$_2$OCH$_2$CH(O)CH$_2$OH     (7)

In an argon atmosphere, a mixture of t-butyl alcohol (41 g), 95 g of a perfluoropolyether represented by HO—CH$_2$CF$_2$CF$_2$O(CF$_2$CF$_2$CF$_2$O)$_n$CF$_2$CF$_2$CH$_2$—OH (number average molecular weight: 1850), potassium t-butoxide (0.8 g), and glycidol (11 g) was stirred at 70° C. for 14 hours. Then, the obtained mixture was washed with water, dehydrated, and then purified by silica gel column chromatography, thereby giving 90 g of Comparative Compound 1 (number average molecular weight: 1936) having two hydroxyl groups (which result from reaction with glycidol) at each terminal.

Comparative Compound 1 was a colorless transparent liquid, and the density of Comparative Compound 1 was 1.75 g/cm³ at 20° C. Comparative Compound 1 was identified by NMR. The results of the NMR are as follows.

$^{19}$F-NMR (solvent: none, reference material: —OCF$_2$CF$_2$CF$_2$O— in the product [−129.7 ppm])

δ=−129.7 ppm [26F, —OCF$_2$CF$_2$CF$_2$O—]
δ=−83.7 ppm [52F, —OCF$_2$CF$_2$CF$_2$O—]
δ=−124.2 ppm [4F, —OCF$_2$CF$_2$CH$_2$OCH$_2$CH(OH)CH$_2$OH],
δ=−86.5 ppm [4F, —OCF$_2$CF$_2$CH$_2$OCH$_2$CH(OH)CH$_2$OH]

$^1$H-NMR (solvent: none, standard substance: D$_2$O)

δ=3.2 to 3.8 ppm [18H, HOCH$_2$CH(OH)CH$_2$OCH$_2$CF$_2$CF$_2$O(CF$_2$CF$_2$CF$_2$O)$_n$CF$_2$CF$_2$CH$_2$OCH$_2$CH(OH)CH$_2$OH]

The results of $^{19}$F-NMR and $^1$H-NMR demonstrate that Comparative Example 1 is a compound represented by Formula (5) where n=13.0.

Comparative Example 2

Comparative Compound 2, which is a fluoropolyether compound having a structure represented by Formula (8) below, was synthesized in the following manner.

HOCH$_2$CH(OH)CH$_2$OCH$_2$CF$_2$CF$_2$O(CF$_2$CF$_2$CF$_2$O)$_m$CF$_2$CF$_2$CH$_2$OCH$_2$CH(OH)CH$_2$CH$_2$—CH$_2$CH$_2$CH(OH)CH$_2$OCH$_2$CF$_2$CF$_2$O(CF$_2$CF$_2$CF$_2$O)$_n$CF$_2$CF$_2$OCH$_2$CH(OH)CH$_2$OH  (8)

In an argon atmosphere, a mixture of t-butyl alcohol (41 g), 95 g of a perfluoropolyether represented by HO—CH$_2$CF$_2$CF$_2$O(CF$_2$CF$_2$CF$_2$O)$_n$CF$_2$CF$_2$CH$_2$—OH (number average molecular weight: 756), potassium t-butoxide (1.4 g), and glycidol (8.8 g) was stirred at 70° C. for 14 hours. The obtained mixture was washed with water, dehydrated, and then purified by silica gel column chromatography, thereby giving 62 g of a perfluoropolyether (number average molecular weight: 830) having one hydroxyl group at one terminal thereof and having two hydroxyl groups (which result from reaction with glycidol) at the other terminal thereof. This compound (60 g) was dissolved in meta-xylene hexafluoride (60 g), and sodium hydroxide (7.0 g) and 1,7-octadienediepoxide (4.3 g) were added thereto, followed by stirring at 70° C. for 14 hours. The obtained mixture was washed with water, dehydrated, and then purified by distillation, thereby giving 50 g of Comparative Compound 2.

Comparative Compound 2 was a colorless transparent liquid, and the density of Comparative Compound 2 was 1.74 g/cm³ at 20° C. Comparative Compound 2 was identified by NMR. The results of the NMR are as follows.

$^{19}$F-NMR (solvent: none, reference material: —OCF$_2$CF$_2$CF$_2$O— in the product [−129.7 ppm])

δ=−129.7 ppm [14F, —OCF$_2$CF$_2$CF$_2$O—]
δ=−83.7 ppm [28F, —OCF$_2$CF$_2$CF$_2$O—]
δ=−124.2 ppm [8F, —OCF$_2$CF$_2$CH$_2$OCH$_2$CH(OH)C$_4$H$_8$CH(OH)CH$_2$—, —OCF$_2$CF$_2$CH$_2$OCH$_2$CH(OH)CH$_2$OH]
δ=−86.5 ppm [8F, —OCF$_2$CF$_2$CH$_2$OCH$_2$CH(OH)C$_4$H$_8$CH(OH)CH$_2$—, —OCF$_2$CF$_2$CH$_2$OCH$_2$CH(OH)CH$_2$OH]

$^1$H-NMR (solvent: none, standard substance: D$_2$O)

δ=3.2 to 3.8 ppm [30H, HOCH$_2$CH(OH)CH$_2$OCH$_2$CF$_2$CF$_2$O(CF$_2$CF$_2$CF$_2$O)$_m$CF$_2$CF$_2$CH$_2$OCH$_2$CH(OH)CH$_2$CH$_2$CH$_2$CH$_2$CH(OH)CH$_2$O—CH$_2$CF$_2$CF$_2$O(CF$_2$CF$_2$CF$_2$O)$_n$CF$_2$CF$_2$CH$_2$OCH$_2$CH(OH)CH$_2$O H]

δ=1.1 ppm [8H, HOCH$_2$CH(OH)CH$_2$OCH$_2$CF$_2$CF$_2$O(CF$_2$CF$_2$CF$_2$O)$_m$CF$_2$CF$_2$CH$_2$OCH$_2$CH(OH)CH$_2$CH$_2$CH$_2$CH$_2$CH(OH)CH$_2$O—CH$_2$CF$_2$CF$_2$O(CF$_2$CF$_2$CF$_2$O)$_n$CF$_2$CF$_2$CH$_2$OCH$_2$CH(OH)CH$_2$O H]

The results of $^{19}$F-NMR and $^1$H-NMR demonstrate that Comparative Example 2 is a compound represented by Formula (6) where n=m=3.5.

[Results of Evaluations of Siloxane Resistance and Heat Resistance]

The compounds obtained in Examples 1 to 4 and Comparative Examples 1 and 2 were evaluated for their siloxane resistance and heat resistance. The results of the evaluations of siloxane resistance and heat resistance are shown in Tables 1 and 2, respectively.

TABLE 1

| | Compound | Amount of attached D4 (ppm) | Amount of lubricant adsorbed on graphite (wt %) |
|---|---|---|---|
| Example 1 | Compound 1A | 881 | 2.0 |
| | Compound 1B | 872 | 2.1 |
| | Compound 1C | 859 | 2.3 |
| Example 2 | Compound 2A | 650 | 2.3 |
| | Compound 2B | 630 | 2.2 |
| | Compound 2C | 633 | 2.3 |
| Example 3 | Compound 3A | 716 | 2.4 |
| | Compound 3B | 720 | 2.4 |
| | Compound 3C | 708 | 2.2 |
| Example 4 | Compound 4A | 617 | 2.5 |
| | Compound 4B | 605 | 2.6 |
| | Compound 4C | 630 | 2.2 |
| Comparative Example 1 | Comparative Compound 1 | 2248 | 2.7 |
| Comparative Example 2 | Comparative Compound 2 | 3375 | 2.6 |

TABLE 2

| | Compound | 10% thermal weight loss temperature (° C.) |
|---|---|---|
| Example 1 | Compound 1A | 319 |
| | Compound 1B | 325 |
| | Compound 1C | 342 |
| Example 2 | Compound 2A | 355 |
| | Compound 2B | 360 |
| | Compound 2C | 368 |
| Example 3 | Compound 3A | 331 |
| | Compound 3B | 345 |
| | Compound 3C | 356 |
| Example 4 | Compound 4A | 363 |
| | Compound 4B | 368 |
| | Compound 4C | 375 |
| Comparative Example 1 | Comparative Compound 1 | 243 |
| Comparative Example 2 | Comparative Compound 2 | 279 |

Table 1 indicates that graphite on which any one of the compounds synthesized in Examples 1 to 4 is adsorbed has a lesser amount of D4 attached thereto, as compared to graphite on which any one of the compounds synthesized in Comparative Examples 1 and 2 is adsorbed. This confirmed that a lubricant that contains any one of the compounds synthesized in Examples 1 to 4 has better siloxane resistance than a lubricant that contains any one of the compounds synthesized in Comparative Examples 1 and 2. The siloxane resistance evaluation is to evaluate how easily impurities attach to a protective layer by measuring the amount of attached siloxane, which is a typical contaminant in the production process of a magnetic disk. That is, when a lubricant that contains any one of the compounds synthesized in Examples 1 to 4 is used, the tendency of impurity contamination of the protective layer, which underlies the lubricant layer, is small as compared to when any one of the compounds synthesized in Comparative Examples 1 and 2 is used. Thus, it can be said that a lubricant that contains any one of the compounds synthesized in Examples 1 to 4 is more resistant to contamination than a lubricant that contains any one of the compounds synthesized in Comparative Examples 1 and 2.

Furthermore, it was confirmed from Table 2 that a lubricant that contains any one of the compounds synthesized in Examples 1 to 4 experiences thermal weight loss at a hither temperature than a lubricant that contains any one of the compounds synthesized in Comparative Examples 1 and 2, and that the lubricant that contains any one of the compounds synthesized in Examples 1 to 4 is more heat resistant than the lubricant that contains any one of the compounds synthesized in Comparative Examples 1 and 2.

INDUSTRIAL APPLICABILITY

A fluoropolyether compound in accordance with an embodiment of the present invention, even when placed on a protective layer so as to form a thin lubricant layer, prevents or reduces the attachment of impurities on the protective layer and also is highly heat resistant. The fluoropolyether compound is therefore suitable for use as a lubricant for a magnetic disk.

REFERENCE SIGNS LIST 1 magnetic disk
2 lubricant layer
3 protective film layer (protective layer)
4 recording layer
5 lower layer
6 soft magnetic lower layer
7 adhesive layer
8 non-magnetic substrate

The invention claimed is:

1. A fluoropolyether compound having a structure represented by Formula (1) below:

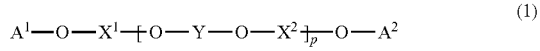  (1)

where $X^1$ and $X^2$ independently represent —$CH_2(CF_2)_qO(CF_2O)_x(CF_2CF_2O)_y(CF_2CF_2CF_2O)_z(CF_2CF_2CF_2O)_w(CF_2)_qCH_2$—, where x and y are each a real number of 0 to 30, z is a real number of 0 to 30, w is a real number of 0 to 20, and q is an integer of 1 to 3,
$A^1$ and $A^2$ independently represent —OH, —$CH_2CH(OH)CH_2OH$, —$OCH_2CH(OH)CH_2OCH_2CH(OH)CH_2OH$, —$O(CH_2)_mOH$, or —$OCH_2CH(OH)CH_2$—$OC_6H_4$—$R^1$, where m is an integer of 2 to 8 and $R^1$ is hydrogen, a $C_1$-$C_4$ alkoxy group, an amino group, or an amide residue,
Y represents a linking group, wherein the linking group has a structure represented by Formula (2) below:

—$CH_2CH(OH)$—R—$CH(OH)CH_2$—  (2), where R represents a $C_1$-$C_6$ aliphatic hydrocarbon group or a $C_6$-$C_{10}$ hydrocarbon group whose main chain contains a phenylene group, at least one carbon atom in the main chain, which contains a phenylene group, of the $C_6$-$C_{10}$ hydrocarbon group is optionally substituted with an oxygen atom, and
p is a real number of 2 or more.

2. The fluoropolyether compound according to claim 1, wherein p in Formula (1) is a real number of 2 to 10.

3. A fluoropolyether compound having a structure represented by any of Formulas (3) to (6) below:

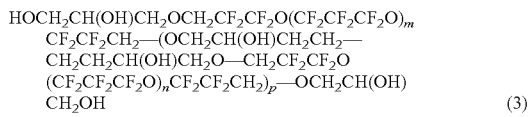  (3)

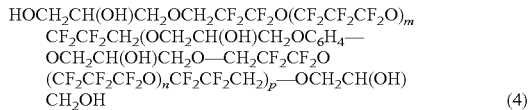  (4)

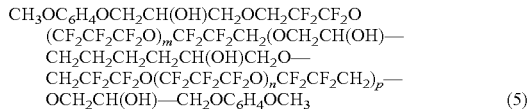  (5)

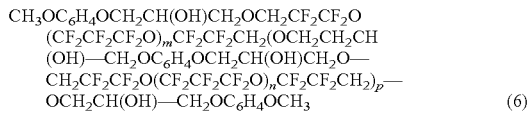  (6)

where n is a real number of 0 to 30, m is a real number of 0 to 30, and p is a real number of 2 to 10.

4. A lubricant comprising a fluoropolyether compound recited in claim 1.

5. A magnetic disk comprising: a recording layer; a protective layer disposed on the recording layer; and a lubricant layer disposed on the protective layer,
the lubricant layer comprising a lubricant recited in claim 4.

6. A method of producing a magnetic disk that includes: a recording layer; a protective layer disposed on the recording layer; and a lubricant layer disposed on the protective layer,
the method comprising a step of forming the lubricant layer by placing a lubricant recited in claim 4 on an exposed surface of the protective layer of a stack of the recording layer and the protective layer.

* * * * *